United States Patent [19]

Anderson

[11] Patent Number: 4,802,612
[45] Date of Patent: Feb. 7, 1989

[54] SPORTING APPARATUS SUPPORT DEVICE FOR THE HANDICAPPED

[76] Inventor: Emmett L. Anderson, 2992 Herrin Rd., #10, Helena, Mont. 59601

[21] Appl. No.: 191

[22] Filed: Jan. 2, 1987

[51] Int. Cl.⁴ .............................................. A01K 97/10
[52] U.S. Cl. .................................... 224/208; 224/200; 224/908; 224/922; 224/913
[58] Field of Search ............... 224/200, 208, 247, 185, 224/913, 922, 908, 205; 43/25

[56] References Cited

U.S. PATENT DOCUMENTS

| | | |
|---|---|---|
| 507,481 | 10/1893 | Brooks . |
| 921,900 | 5/1909 | Shuster .......................... 224/247 X |
| 1,198,202 | 9/1916 | Drinkard ....................... 224/922 X |
| 2,271,136 | 1/1942 | Geiger . |
| 2,537,456 | 1/1951 | Goss ................................... 224/200 |
| 2,658,650 | 11/1953 | Jasper . |
| 2,709,544 | 5/1955 | Barringer . |
| 2,742,211 | 4/1956 | Craft, Sr. ....................... 224/922 X |
| 2,995,855 | 8/1961 | Bell . |
| 3,090,621 | 5/1963 | Heimers et al. ................ 224/200 X |
| 3,191,826 | 6/1965 | Adams ................................ 224/185 |
| 3,501,074 | 3/1970 | Emerick ......................... 224/913 X |
| 3,661,308 | 5/1972 | Walters ............................... 224/908 |
| 4,081,115 | 3/1978 | White et al. . |

Primary Examiner—Henry J. Recla
Assistant Examiner—Linda J. Sholl
Attorney, Agent, or Firm—William D. West

[57] ABSTRACT

A sporting apparatus support device for the handicapped having a front support plate and a back support plate which are adjustably attached to each other with belts so as to securely sandwich the wearer is disclosed. An across-the-shoulder strap extending from the front support plate to the back support plate is also provided and an outwardly and upwardly extending bar from the front support plate is provided for attaching a fishing rod holder, a gun rest, or a camera support. A pivotal bar rod lock and a line and hook vise is also disclosed.

13 Claims, 2 Drawing Sheets

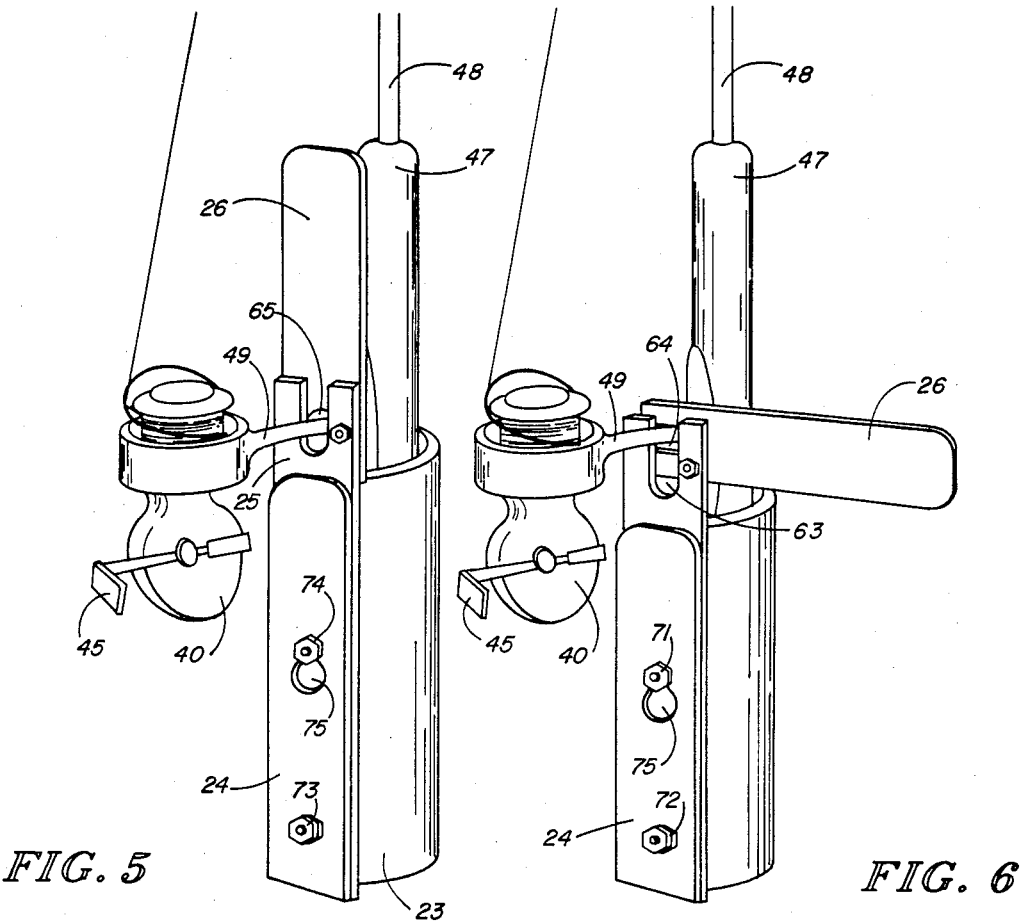
FIG. 5
FIG. 6
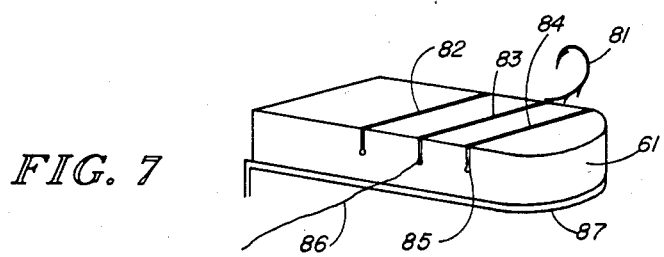
FIG. 7
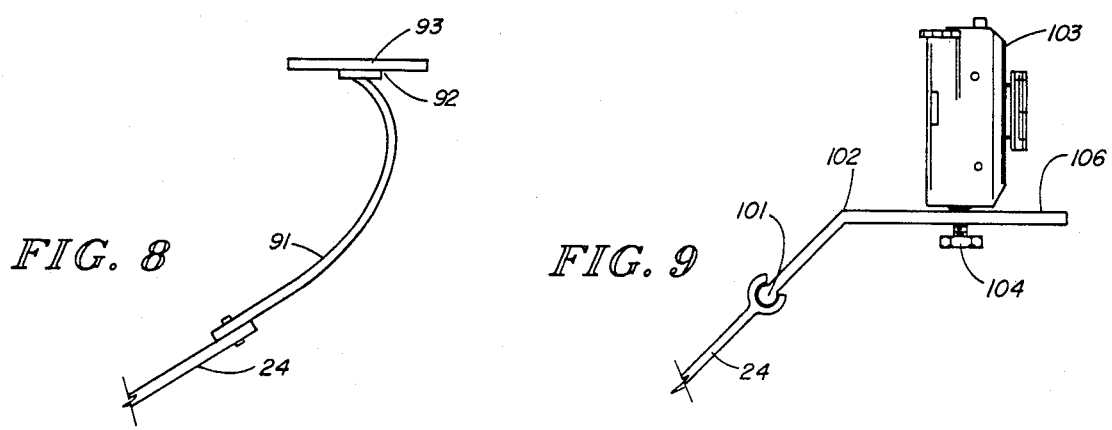
FIG. 8
FIG. 9

SPORTING APPARATUS SUPPORT DEVICE FOR THE HANDICAPPED

BACKGROUND OF THE INVENTION

1. Field of the Invention

The invention relates to a sporting apparatus support device for the handicapped, and in particular to a device which allows a person having the use of only one arm to enjoy the sports of fishing, photography, and shooting.

2. Discussion of the Technical Problems

Recreational fishing is a popular pastime. Increasingly greater numbers of people are now enjoying the outdoors through the sport of fishing. Spin casting, fly fishing, and other forms of the sport are enjoyed by millions of people in all walks of life. Unfortunately, people who have only the use of one hand whether by accident, disease, injury, or any other means are not able to fully enjoy the sport of fishing since the operation of a fishing pole including the casting, reeling, baiting of hooks, tying on of lures, and the like require the use of two hands, one to hold the pole and the other to manipulate the line or lure.

Handicapped people who have lost the use of one hand or arm are also restrained from enjoying the pursuits of photography and hunting or target shooting. It is difficult to hold a camera or gun while still activating the shutter release or trigger.

In order to engage in the sport of fishing, it has been found that handicapped people having the use of only one arm have been able to use rod-holding attachments which can be pushed into the ground or attached to the side of a boat or dock. In addition, attempts have been made to provide a rod-holding device attached to a person's belt. One such device for attaching to a person's belt is U.S. Pat. No. 2,537,456 to Goss issued Jan. 5, 1951. In the Goss invention, the belt-supported rod support is further attached to the person by a lanyard about his neck.

An attempt to provide a fishing rod holder integral with a belt is disclosed in U.S. Pat. No. 2,658,650 to Jasper issued Nov. 10, 1953. Another type of rod and reel holder designed for the use of persons having only one arm is shown in U.S. Pat. No. 2,709,544 to Barringer issued May 31, 1955.

Unfortunately, all of the prior art fishing rod holders designed for people having only the use of one arm lack sufficient stability to grasp the rod so that a person having only one arm can adequately reel in a fish and yet can easily remove the rod from the holder. Furthermore, prior art devices provide no means for total adjustment and no means to use the device for other pursuits such as photography or hunting.

The ideal fishing rod support device for the handicapped would provide a stable belt that could be worn other than only at the waist. It would employ a number of adjustments and straps to adequately secure the device to a person's body and it would provide a secure, positive rod-holding apparatus. Such a device should be adaptable to allow a person to use the device for photography and for providing a rest for shooting so that the device can have many uses other than simply as a fishing rod holder. The ideal device should also provide an attachment which would allow a person having only one hand to change lures, bait a hook, and load a camera.

No known examples of a sporting apparatus support device for the handicapped which allows a person to fish with a stable platform have been discovered and none known are directed to providing such a support device which would allow its use for other sporting pursuits such as hunting or photography.

Accordingly, a need exists for a sporting apparatus support device for the handicapped that would provide a safe, convenient, stable, secure, and easily adjustable fishing rod holder that could be easily converted to a camera holder or gun rest. Such a device would provide a simple, inexpensive apparatus that could be easily adapted to different sizes of people. It should also provide a holding attachment so that a hook could be baited, line could be tied, lures could be changed, and the like. A device of that type would be simple in design, easy to maintain, and easy to put on and take off. Such a device should be easily repaired, not subject to damage by proper use, and simple to manufacture. The instant invention is directed to all these needs as well as others as explained in the following summary.

SUMMARY OF THE INVENTION

It is a feature of the invention to provide a sporting apparatus device for the handicapped.

It is another feature of the instant invention to provide a device which allows a person having the use of only one arm to ejoy the sports of fishing, photography, and shooting.

It is another feature of the instant invention to provide a device to aid the handicapped in the sports of fishing, photography, and shooting that provides a front support plate and a back support plate, at least one belt connecting a front support plate with a back plate, and an over-the-shoulder support belt.

It is another feature of the instant invention to provide a sporting apparatus support device for the handicapped which is securely adjustably attached to the person's body and provides an extended fishing rod holder.

It is another feature of the instant invention to provide a sporting apparatus support device for the handicapped which is securely adjustably attached to the person's body and provides an extended camera holder.

It is another feature of the instant invention to provide a sporting apparatus support device for the handicapped which is securely adjustably attached to the person's body and provides an extended gun rest.

It is yet another feature of the instant invention to provide a sporting apparatus support device for the handicapped having a line and hook-holding vise.

These and other features and objects are attained according to the instant invention by providing a sporting apparatus support device for the handicapped having a front support curved plate; a back support curved plate, two adjustable web belts attaching the front support plate to the back support plate, and an adjustable web belt extending from the front support belt over the shoulder of the wearer to the back support plate. The device also includes a rigid extendible elongate bar having a length of flexible tubing attached so that the bar and the tubing extend away from the wearer's body. A pivotal elongate bar having a notch which co-acts with a notch in the first bar extending away from the wearer's body to hold a fishing rod securely is also provided. A line-holding attachment having an extendible platform attached to the front support plate above the fishing rod holder and having a number of kerfs to hold a line and hook securely for the baiting of same is provided. In another embodiment, a curved pivotally attached elongate rest is provided attached to the first elongate bar to provide a rest for shooting a pistol, rifle or shotgun. In a further embodiment, a ball swivel is provided having an extension adaptable for connection to a camera. The device is further provided with multiple adjustments.

BRIEF DESCRIPTION OF THE DRAWINGS

The advantages of this invention will become apparent upon consideration of the following detailed disclosure of the invention, especially when taken in conjunction with the accompanying drawings, wherein:

FIG. 5 is a partial perspective view of the locking adapter of the rod-holder in accordance with the present invention.

FIG. 6 is a partial perspective view of the locking adapter of the rod-holder in accordance with the present invention with the locking bar being moved from a locked position to an unlocked position.

FIG. 7 is a detailed perspective view of the line and hook-holding vise showing a hook in position for baiting in accordance with the present invention.

FIG. 8 is a second embodiment of the invention depicting an elongate extension for use as a gun rest.

FIG. 9 is a further embodiment of the invention depicting an elongate swivel attachment for use as a camera rest, all in accordance with the present invention.

DESCRIPTION OF THE PREFERRED EMBODIMENT

Figure 1:
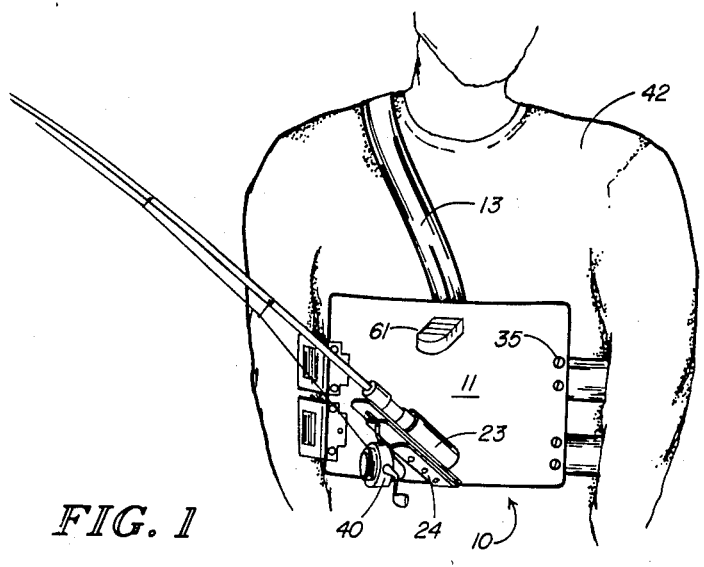
FIG. 1 is a front perspective view of the sporting apparatus support device for the handicapped shown holding a spin casting rod in accordance with the present invention.

The sporting apparatus support device for the handicapped of the instant invention is depicted generally in FIG. 1 attached to a user. First of all, it should be noted that the device is not limited to use by a person who has lost a hand or arm, but is suited primarily for people who have lost the use of a hand or arm. Many times people who have suffered mild strokes and the like have found that they have lost part or all of the function of one hand or arm. The device of the present invention is ideally suited for such a person.

Figure 2:
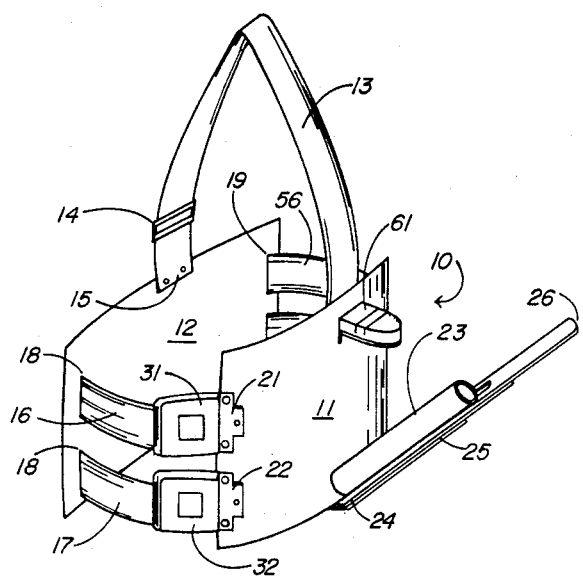
FIG. 2 is a side elevational view of the sporting apparatus support device for the handicapped in which no wearer is shown and the device is rigged for fishing.

As can be seen by reference to FIGS. 1 and 2, the device provides a front support plate 11 which is a curved flat plate. The front support plate 11 is curved to adapt to the natural curvature of the body and extends upwardly from the waist area to the midriff section of the wearer and from side to side not entirely to the edge of the rib area.

Figure 4:
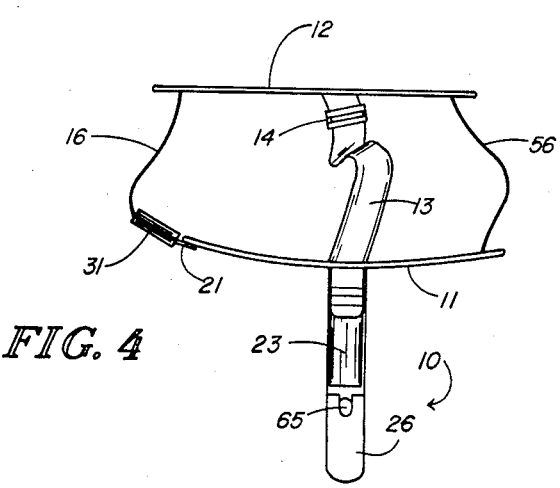
FIG. 4 is a top plan view of the sporting apparatus support device for the handicapped in accordance with the present invention.

As can be seen by reference to FIGS. 2 and 4, a back support plate 12 is also provided which can be curved to conform to the back of the body as shown in FIG. 2 or straight as shown in FIG. 4. The front support plate 11 and the back support plate 12 effectively sandwich the wearer's lower torso.

Figure 3:
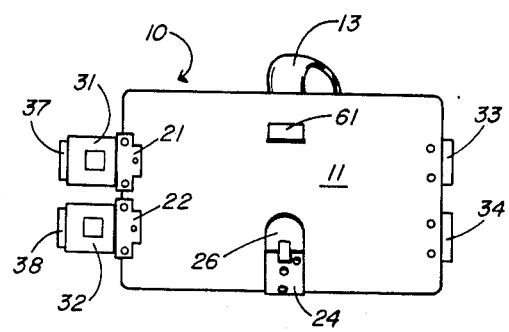
FIG. 3 is a front elevational view of the sporting apparatus support device for the handicapped in accordance with the present invention.

As can be seen by reference to FIGS. 1, 2, 3, and 4, front support plate 11 and back support plate 12 are joined by adjustable web belts 16 and 17. Web belts 16 and 17 are attached on one side of front support plate 11 as shown in FIG. 1 by attachment screws or rivets 35 and/or metal attachment plates 33 and 34 as shown in FIG. 3. The belts 16 and 17 extend from front support plate 11 in parallel fashion as depicted in FIG. 2 to pass through slits 19 and are re-routed through the opposite side of back support plate 12 through slits 18 where they terminate in quick release connections 31 and 32 which fit into quick release attachment sections 21 and 22 on front support plate 11 in the same manner as an automobile seat belt. In fact, it has been found that an automobile seat belt provides a very secure adjustable tensioning belt for the device of the instant invention and it is a belt that is easily released as well as tightened and the maintenance and repair of the mechanism of the quick release 31 and 32 is well known. It has been found that the use of a single belt device does not have a sufficient amount of stability and support that is provided by the use of multiple belts. Multiple belts also provide for the different diameters about a person's body at the different areas where the belts are tightened.

It can further be seen by reference to FIG. 1, 2, 3, and 4 that cross shoulder support strap 13 is provided. Cross shoulder support belt 13 is attached to the upper portion of upper edge of front support plate 11 and is routed so as to go over the shoulder of a wearer 42 and is then attached to the back support plate 12 in a manner that is well known in the art such as the use of rivets, screws, or other fasteners. The cross shoulder support belt 13 can be provided with an adjustment tensioning chip 14 in a manner well known in the art. It is also apparent from FIG. 1 that the across the shoulder support belt 13 could be placed on either the right or the left shoulder of wearer 42, depending on whether or not the wearer 42 wished to use his right or left hand in operating the device. In another embodiment not shown, it has been noted that the placement of the release attachments 31 and 32 could be on the opposite side so that a person wishing to release the belts by the other hand would be able to do so. The embodiment as depicted in FIGS. 1 through 4 is designed for use by a person having the use of their left hand and arm.

As can be seen by reference to FIGS. 2, 3, and 4, the device is further provided with an extendible elongate flattened bar 25 which is rigidly attached to front support plate 11 and extends upwardly and outwardly from the wearer as shown in FIGS. 1, 2, 3, and 4. Attached to the upwardly extending bar 24 is fishing support bar 25 and fishing rod support holding cylinder 23. Fishing rod support holding cylinder 23 is rigidly attached to support bar 25; however, support bar 25 and elongate bar 24 are bolted together as depicted in FIGS. 5 and 6. It is readily apparent that by loosening the nuts 73 and 74 as depicted in FIG. 5 that fishing rod support bar 25 and associated rod support cylinder 23 can be removed from the device and any other sporting apparatus such as a gun rest as depicted in FIG. 8 or a camera rest as depicted in FIG. 9 can be attached.

As can be seen in FIGS. 1, 2, 3, and 4, an additional attachment 61 is provided which in the preferred embodiment is a wooden block having saw cuts or kerfs which serve as a vise. With careful reference to FIG. 7, it can be seen that the vise is further provided with a metal support shelf 87 which is rigidly attached to front support plate 11 in a cantilever fashion and line and hook vise 61 is further provided with slits 82, 83, and 84 and cylindrical holes 85 which allow a line 86 to be placed within the slit 83, for example, and pulled taut until the eyelet of hook 81 engages the hole 85 and holds hook 81 so that hook 81 is held securely for baiting purposes.

The structures of front support plate 11 and back support plate 12 are preferably metal; however, any convenient material such as fiberglass could be used with varying results. It has been shown that aluminum is sufficiently lightweight and rigid to be of durable material; however, it should be covered with a naugahyde or leather or other similar material and provided with padding in order to provide comfort to the wearer.

With reference to FIGS. 5 and 6 where the device is shown attached to a fishing rod holder, a novel fishing rod locking device is shown. As can be seen with reference to FIG. 5, fishing rod 48 having handle 47 and reel 40 with reel support 49 extending from reel 40 to rod handle 47. Extendible elongate bar 24 which is rigidly attached to front support plate 11 as depicted in FIGS. 1, 2, 3, and 4 is removably attached by means of bolts and nuts 73 and 74. Rod holding bar 25 is provided with an open slit 65 which allows the reel support rod 49 to fit within. Locking bar 26 is pivotally attached to one side of rod holding bar 25. Locking bar 26 is also provided with a co-acting slit 64 as depicted in FIG. 6 which, when placed about reel support bar 49 and placed in the upward locking position as shown in FIG. 5 (paralleling fishing rod 4) securely locks the reel support bar 49 in position. Prior to locking the reel support bar 49 as shown in FIG. 5, it is necessary to place the handle 47 of fishing rod 48 in the cylindrical rod holder 23. Cylindrical rod holder 23 is a cylinder made of any convenient material. It has been found that a flexible material such as a length of rubber radiator hose provides a sufficient amount of rigidity and yet is flexible enough to be adapted to any number of rods and rod handles. The cylindrical rod holder 23 is rigidly attached by any means such as screws, bolts, gluing or rivets to rod holding bar 25 as shown in FIGS. 5 and 6.

As previously discussed, further embodiments such as the gun rest depicted in FIG. 8 can be easily adapted to the sporting apparatus support device for the handicapped 10 by simply attaching additional extensions 91 as depicted in FIG. 8 having a support bar 92 and rest 93. By having a pivotal attachment as depicted in FIG. 8, curved support rest bar 91 can be moved right or left so that the gun rest 93 is in the proper position for the use of the wearer.

If a person having only the use of one hand or arm wishes to engage in the sport of photography, it would be quite possible to adapt the device of the instant invention by providing a camera support swivel 101 attached to extendible bar 24. The swivel attachment 101 as depicted in FIG. 9 could also be utilized for a camera support or for a fishing rod holder of any other type. As shown in FIG. 9, camera 103 is further removably attached by means of attachment 104 to movable extendible rod 106 to provide a stable rest for the user.

Although specific applications, materials, components, connections, sequences of events, and methods have been stated in the above description of the preferred embodiment of the invention, other suitable materials, other applications, components and process steps as listed herein may be used with satisfactory results and varying degrees of quality. In addition, it will be understood that various other changes in details, materials, steps, arrangements of parts and uses which have been herein described and illustrated in order to describe the nature of the invention will occur to and may be made by those skilled in the art, upon a careful reading of this disclosure, and such changes are intended to be included within the principles and scope of this invention as hereinafter claimed.

I claim:

1. A sporting apparatus support device for the handicapped comprising:
   a substantially rectangular front body support plate having an upper portion, a lower portion, and either sides, and an elongate attachment bar extending upwardly and outwardly from the lower portion of said front support plate;
   a transverse belt means for attachment around the torso of the wearer, said belt means attached to and extending from either side of said front support plate;
   a back support plate having an upper portion, a lower portion, and either side; said back support plate attached to said belt means;
   a fishing rod holder means removably attached to said attachment bar; and
   a line-holding mans attached to the upper portion of said front support plate wherein said line-holding means comprises an outwardly extending projection having at least one kerf.

2. The sporting apparatus support device for the handicapped as described in claim 1 further comprising at least one transverse hole in said kerf.

3. A sporting apparatus support device for the handicapped as described in claim 1 wherein said belt means comprises two belts in spaced parallel relationship extending from either sides of said front support plate.

4. A sporting apparatus support device for the handicapped as described in claim 3 wherein said belts are automobile seat belts.

5. The sporting apparatus support device for the handicapped as described in claim 1 further comprising a gun rest means removably attached to said attachment bar.

6. The sporting apparatus support device for the handicapped as described in claim 1 further comprising a camera support means removably attached to said attachment bar.

7. A sporting apparatus support device for the handicapped as described in claim 1 further comprising adjustable tension means attached to said belt means.

8. A sporting apparatus support device for the handicapped as described in claim 1 further comprising an upper shoulder belt extending from the upper portion of said front support plate to the upper portion of said back support plate.

9. The sporting apparatus support device for the handicapped as described in claim 8 wherein said upper shoulder belt is adjustable in length.

10. The sporting apparatus support device for the handicapped as described in claim 9 further comprising a reel lock attached to said attachment bar.

11. The sporting apparatus support device for the handicapped as described in claim 10 wherein said reel lock is comprised of a pair of pivotally attached bars having a pair of co-acting slits to accommodate and lock a support bar of a reel.

12. The sporting apparatus support device for the handicapped as described in claim 9 wherein said fishing rod holder means comprises a cylinder adapted to accept a fishing rod holder.

13. The sporting apparatus support device for the handicapped as described in claim 12 wherein said cylinder is made of a flexible material.

* * * * *